(12) United States Patent
Simon

(10) Patent No.: US 9,044,283 B2
(45) Date of Patent: Jun. 2, 2015

(54) BONE NAIL WITH SMOOTH TRAILING END

(71) Applicant: Stryker Trauma GmbH, Schönkirchen (DE)

(72) Inventor: Bernd Simon, Kiel (DE)

(73) Assignee: Stryker Trauma GmbH (DE)

( * ) Notice: Subject to any disclaimer, the term of this patent is extended or adjusted under 35 U.S.C. 154(b) by 0 days.

(21) Appl. No.: 13/755,711

(22) Filed: Jan. 31, 2013

(65) Prior Publication Data
US 2014/0214035 A1 Jul. 31, 2014

(51) Int. Cl.
*A61B 17/72* (2006.01)
*A61B 17/74* (2006.01)

(52) U.S. Cl.
CPC .................... *A61B 17/744* (2013.01)

(58) Field of Classification Search
CPC ............. A61B 17/72; A61B 17/7233; A61B 17/7241; A61B 17/7283; A61B 17/74; A61B 17/742; A61B 17/744
USPC ..................................... 606/62–68
See application file for complete search history.

(56) References Cited

U.S. PATENT DOCUMENTS

| | | | |
|---|---|---|---|
| 5,176,681 A | 1/1993 | Lawes et al. | |
| 5,429,640 A * | 7/1995 | Shuler et al. | 606/64 |
| 5,480,402 A | 1/1996 | Kim | |
| 6,053,918 A | 4/2000 | Spievack | |
| 6,443,954 B1 | 9/2002 | Bramlet et al. | |
| 7,232,442 B2 * | 6/2007 | Sohngen et al. | 606/62 |
| 7,601,153 B2 | 10/2009 | Shinjo et al. | |
| 7,763,022 B2 | 7/2010 | Speitling et al. | |
| 7,901,410 B2 * | 3/2011 | Bigdeli-Issazadeh et al. | 606/98 |
| D638,126 S | 5/2011 | Velikov | |
| 8,337,505 B2 | 12/2012 | Bigdeli-Issazadeh et al. | |
| 8,709,055 B2 | 4/2014 | Beyar et al. | |
| 2005/0055024 A1 * | 3/2005 | James et al. | 606/64 |
| 2005/0216027 A1 | 9/2005 | Suh et al. | |
| 2011/0137312 A1 * | 6/2011 | Mantovani et al. | 606/63 |

FOREIGN PATENT DOCUMENTS

| | | | | |
|---|---|---|---|---|
| EP | 118778 A1 * | 9/1984 | | A61B 17/18 |
| EP | 0471419 A2 | 2/1992 | | |
| EP | 0 738 502 A2 * | 10/1996 | | A61B 17/72 |
| EP | 0738502 A2 | 10/1996 | | |
| GB | 2421187 A | 6/2006 | | |

(Continued)

OTHER PUBLICATIONS

English Translation of EP 118778 A1; accessed from Espacenet.com on Sep. 19, 2014.*

(Continued)

*Primary Examiner* — Eduardo C Robert
*Assistant Examiner* — Julianna N Harvey
(74) *Attorney, Agent, or Firm* — Lerner, David, Littenberg, Krumholz & Mentlik, LLP

(57) ABSTRACT

A bone nail has a shaft with a leading section and a trailing section, wherein the trailing section includes an end surface having at least one depressed portion and at least one elevated portion. The transition between one of the depressed portions and the adjacent elevated portion is smooth. The end surface is formed so as to transmit rotational forces as well as translational forces from a medical device to the shaft of the bone nail, when the medical device is coupled at the end surface to the trailing section of the bone nail.

16 Claims, 2 Drawing Sheets

(56) References Cited

FOREIGN PATENT DOCUMENTS

| | | | |
|---|---|---|---|
| JP | 2005205201 | A | 8/2005 |
| JP | 2007530149 | A | 11/2007 |
| JP | 2012515038 | A | 7/2012 |

OTHER PUBLICATIONS

Japanese Office Action for Application No. 2014-011939 dated Jan. 6, 2015.

* cited by examiner

BONE NAIL WITH SMOOTH TRAILING END

BACKGROUND OF THE INVENTION

The invention relates to an implant. In particular, the invention relates to a bone implant like a bone nail.

An implant and particularly a bone implant includes a portion or section or end which is adapted to be first introduced into a body during implantation. In this specification, such a portion or section or end is referred to as leading portion or leading section or leading end. Consequently, an opposite portion or section or end of the implant is adapted to be introduced last, wherein this portion or section or end may additionally be configured for an engagement of a tool for inserting the implant into the body. Below, such a portion or section or end is referred to as trailing portion or trailing section or trailing end.

A bone implant may be a pin or a nail or screw. A bone nail may be an intramedullary nail, for example a femur nail, a humerus nail or a tibia nail. A bone screw may be a screw for fixing fragments of a bone fracture or may be a locking screw for locking a bone nail in the bone.

However, due to the anatomical variation of bones it may happen that the trailing end of a bone implant protrudes above the bone surface. The trailing end of the implant may act as an interface towards a target or aiming device. In order to create a solid fixation, nails may be provided with grooves in order to fit pegs on a post of a target device for accurate alignment, for sufficient fixation, and for controlling the forces applied during implant insertion and removal. It may occur that patients complain about pain after surgery in this area, especially when the implant trailing end is sticking out of the bone. This pain may be caused by sharp edges at the trailing end of the implant. Such edges may cause irritation and/or injury to the surrounding soft tissue.

U.S. Pat. No. 7,763,022 discloses a typical prior art intramedullary nail.

U.S. Pat. No. 6,443,954 B1 describes an intramedullary nail for securing portions of a bone together. A lag screw may extend through a radial bore in the nail. Furthermore, a cap screw may be screwed into the trailing end of the nail for holding the lag screw, wherein this lag screw has a spherical head portion.

BRIEF SUMMARY OF THE INVENTION

One aspect of the invention may be defined as providing an implant causing less irritations of surrounding tissue when being implanted.

This is achieved by the subject-matter of the independent claim. Further embodiments are described in the dependent claims.

In general, an implant, in particular a bone nail comprises a shaft with a leading section and a trailing section, wherein the trailing section includes an end surface having at least one depressed portion and at least one elevated portion, wherein a transition between one of the depressed portions and the adjacent elevated portion is smooth. The end surface is formed so as to transmit rotational forces as well as translational forces from a medical device to the shaft of the implant, when the medical device is coupled at the end surface to the trailing section of the implant. The medical device may be a targeting device as shown in U.S. Pat. No. 5,176,681 but with a shape adapted to mate with the end of the nail of the present invention.

It will be understood that "smooth" refers to a shape without any edges, in particular without any sharp edges. That is, the end surface is formed without any discontinuities. The edge between the end surface and an circumferential outer surface of the implant may be provided with a chamfer or may be rounded so as to be also smooth, i.e. so as to not form any edge at which irritations of soft tissue may occur when the tissue is in contact with the trailing section of the implant including the end surface.

According to one embodiment, the end surface describes a waveform along the circumference of the shaft, wherein the waveform may be a sinusoidal waveform. The waveform extends in the direction of a longitudinal axis of the nail trailing end. The outer circumference at the targeting end may be generally cylindrical.

It is noted that the waveform may have only one depressed portion and one elevated portion so that the end surface may be formed like a bevel or a slanted surface relative to a longitudinal axis of the implant.

According to one embodiment, the end surface includes two or more depressed portions with elevated portions between the two or more depressed portions, respectively.

The following advantages may be achieved by an end surface having a waveform:
  Impingement of the surrounding tissue may be reduced.
  A contour may be formed which fits to the surface of the bone.
  Stress may be reduced in the region between implant and tool, allowing for a metal to plastic material interface which permits smaller dimensions and possibly cost reduction.
  During assembly, the implant and tool may be easily self-centering.
  An accurate play-free interface is possible.

According to another embodiment, the end surface corresponds to a shape of an outer bone surface at an intended implantation site so that the end surface of the implant may be flush with the bone surface surrounding the end surface when the implant is inserted into the bone. Depending from the intended implantation site, for example the femur head, the end surface may have a complex waveform with differing depressed portions and differing elevated portions.

An exemplary bone implant may be an intramedullary nail comprising a through bore for receiving a locking screw, the through bore extending through the shaft in a direction transverse but also inclined relative to a longitudinal axis of the shaft. The depressed portion of the end surface may have a deepest or lowest point, wherein the deepest or lowest point may be aligned with the axis of the through bore.

The bone implant may also be a bone screw. For example, the bone screw may be a locking screw which may be received in a transverse through bore in the shaft of an intramedullary nail. As the bone screw may be inserted with an inclined angle (being not perpendicular) to an axis of the bone, or at least angled relative to the outer surface of the bone, the trailing end of the bone screw may comprise an end surface with a waveform or undulating form corresponding to the shape of the outer surface of the bone at the point or area of introduction of the screw. Thus if the bone outer surface is cylindrical then the screw receiving end would have high and low points matching the bone surface.

According to a further embodiment, the implant further comprises a bore formed at least in the trailing end section, with the bore extending in a longitudinal direction of the shaft. The longitudinal bore may include an inner thread for releasably fixing a medical device like a driving tool for manipulating the implant during an implantation or like a targeting device.

Alternatively, the implant may further comprise a longitudinal bore in the trailing end section including a feature of a bayonet connector for releasably fixing a medical device like a driving tool or a targeting device. Accordingly, one or more grooves may be provided in the inner surface of the longitudinal bore each being configured for receiving a pin-like structure. It will be understood that the trailing end of the implant may also comprise pin-like structures for an engagement in bayonet grooves formed at a medical device. Such a structure is shown in U.S. Pat. Nos. 7,901,410 and 8,337,505 assigned to assignee of the present invention. The disclosures of U.S. Pat. Nos. 7,901,410 and 8,337,505 are incorporated herein by reference According to an embodiment, a system is provided having the implant as described above and a medical device with an implant engagement portion having a contact surface which corresponds to the end surface at the trailing section of the implant. The medical device may be an aiming or targeting device for assisting an introduction of a locking screw and/or a driving tool for manipulating the implant during an implantation of the implant.

According to another embodiment, the system may further have an adapter element having a first end adapted to be coupled to the end surface at the trailing end of the implant and a second end adapted to be coupled to the medical device. With an adapter element, it is possible to utilize a usual aiming device or driving tool with an implant having a smooth end surface.

It is noted that a person skilled in the art will gather from the above and the following description that, unless otherwise notified, in addition to any combination of features belonging to one embodiment, also any combination of features relating to another embodiment is considered to be disclosed with this application.

These and other objects, features and advantages of the exemplary embodiments of the present invention will become apparent upon reading the following detailed description of exemplary embodiments, when taken in conjunction with the appended claims.

BRIEF DESCRIPTION OF THE DRAWINGS

The invention will now be detailed by way of exemplary embodiments with reference to the attached drawings.

Figure 1:
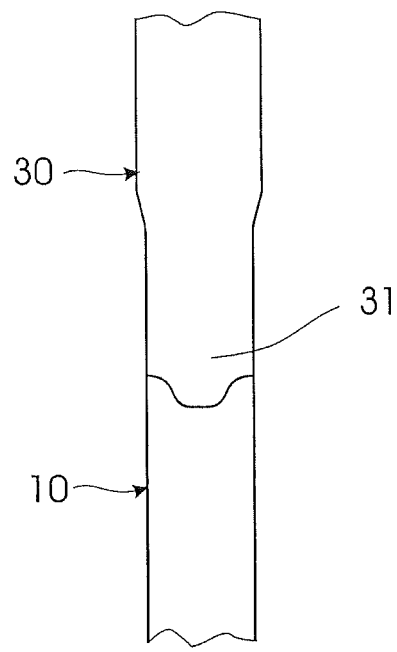
FIG. 1 shows a medical device coupled to a trailing end section of a bone nail.

It is noted that the illustration in the drawings is only schematically and not to scale. Throughout the drawings, the same reference numerals and characters, unless otherwise stated, are used to denote like features, elements, components, or portions of the illustrated embodiments. Moreover, while the present invention will now be described in detail with reference to the FIGS., it is done so in connection with the illustrative embodiments and is not limited by the particular embodiments illustrated in the figures, as defined by the appended claims.

DETAILED DESCRIPTION

Figure 2:
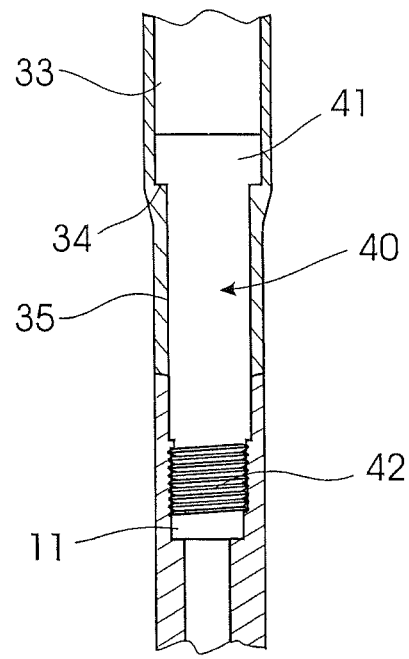
FIG. 2 is a section view of the combination of FIG. 1.

FIGS. 1 and 2 show a trailing section 10 of an implant together with a coupling section 30 of a medical device like a targeting device or a driving tool, or of an adapter element to be placed between the medical device and the implant. The coupling section 30 includes an implant engagement portion 31. The implant engagement portion includes an end surface with a waveform which is complementary to the waveform of the end surface at the trailing section of the implant.

The coupling section further comprises an inner through bore with a first bore section 33 and a second bore section 35. The first bore section has a first diameter and the second bore section has a second diameter, wherein the second diameter is smaller than the first diameter. The transition of the first diameter to the second diameter is formed by a shoulder 34. An axial bore 11 is formed in the trailing section 10 of the implant, wherein this axial bore includes an inner threaded portion.

As shown in FIG. 2, the coupling section 30 may be firmly connected to the trailing section 10 of the implant by means of a fixing screw 40. The fixing screw 40 comprises a screw head 41 and a screw thread 42. The outer diameter of the screw head may fit to the first diameter of the first bore section 33 of the coupling section, i.e. may be slightly smaller, and the outer diameter of the threaded portion 42 may fit to the second diameter of the second bore portion 35 of the coupling section 30, i.e. may be slightly smaller, so that the fixing screw 40 may be received in the bore of the adapter with the screw head 41 resting on the shoulder 34.

The fixing screw has a length so that the fixing screw protrudes out of the coupling section 30 and into the trailing section 10 of the implant so that the screw thread 42 may engage the threaded portion of the axial bore 11 in the trailing section 10. By means of the fixing screw 40, the end surface at the implant engagement portion 31 of the coupling section 30 and the end surface at the trailing section 10 of the implant may be pressed together. By way of this, the coupling section and thus a medical device can be fixed to the implant in a predetermined orientation and the waveform of the fitting end surfaces allow a transmission of forces both in translational direction and in rotational direction. The force affected in axial direction by the fixing screw permits that the end surfaces slide onto each other. In such a configuration, no edges for a force transmission are necessary.

Figure 3:
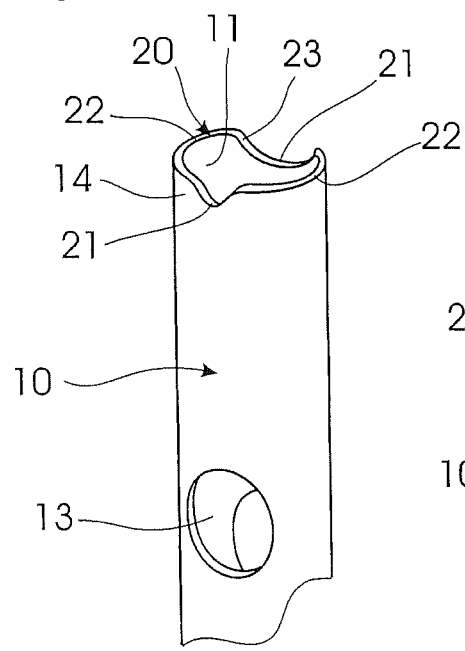
FIG. 3 is an isometric view of a trailing end section of a first embodiment of a bone nail having a wave with two peaks and valleys.
Figure 6:
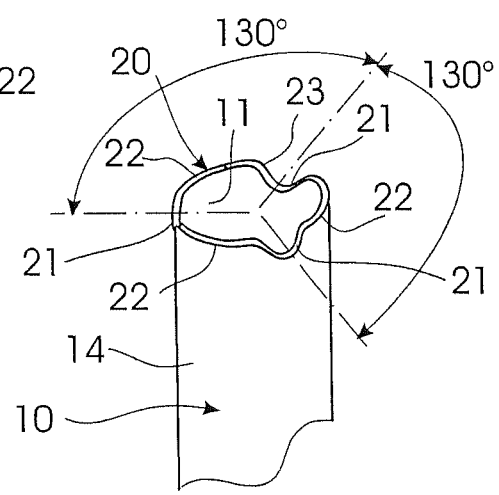
FIG. 6 is an isometric view of a trailing end section of a second embodiment of a bone nail having a wave form with three peaks and valleys.

FIG. 3 shows an isometric view of the trailing end section 10 of a bone nail, and particularly an embodiment of an end surface 20. The end surface 20 is the ring-like surface extending between the inner surface of the axial bore portion 11 and the outer surface 14. In FIG. 3, the end surface 20 includes two depressed portions or valleys 21 and two elevated portions or peaks 22. Each of the transitions 23 between the depressed portions 21 and the elevated portions 22 is smooth. By smooth it is meant there are no sharp corners and, for example, the end surface 20 may be continuously curved. In this embodiment, the depressed portions differ from each other with respect to the width. It will be understood that the portions may also differ from each other with respect to the depth. The end surface 20 is defined by a waveform (for example a sine wave) running on the circumference of the trailing end section of the bone nail, around an opening of an axial bore 11. The end surface 20 can have three or four elevated and depressed portions. The distance from the peaks (elevated portions) to the valleys (depressed portions) may be 2.5 to 3.8 mm. In a three peak design the peaks may be between 100 and 130° apart. In a 15.5 mm proximal diameter nail with three peaks, for example, the peaks would be spaced about 16.23 mm (120°) which is Pi×15.5 mm/3. This embodiment is shown in FIG. 6 where two valleys 21 and peaks 22 are spaced at 130° from one valley 22 and spaced 100° from each other. The combination of angles (120°) can be used. The shape may be a sinusoidal wave.

As further depicted in FIG. 3, the trailing section 10 includes a transverse bore 13 defining an axis. The deepest point of the depressed portion 21 may be aligned with the axis of the transverse bore 13. Thus, the coupling section 30 has a predetermined orientation relative to the trailing end section of the bone nail. This may in particular be of interest when an aiming or targeting device should be coupled to the bone nail.

Figure 4:
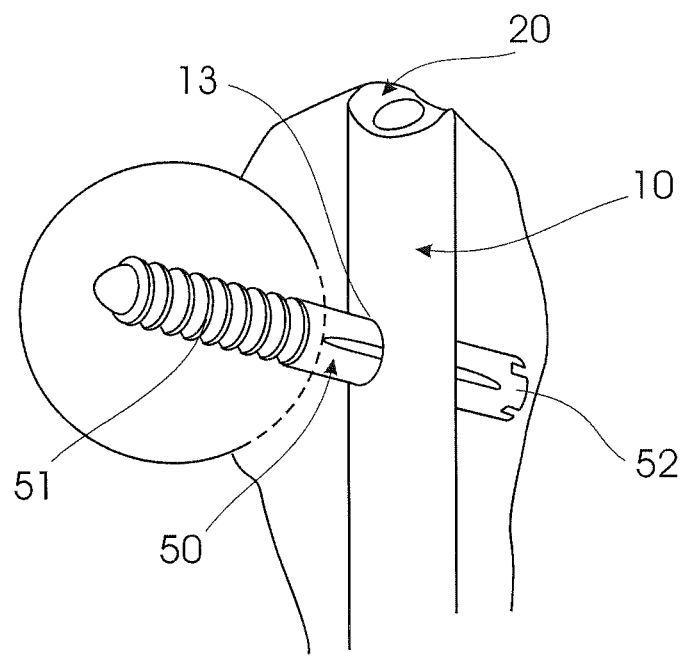
FIG. 4 is an isometric illustration of an intramedullary nail in a femur.
Figure 5:
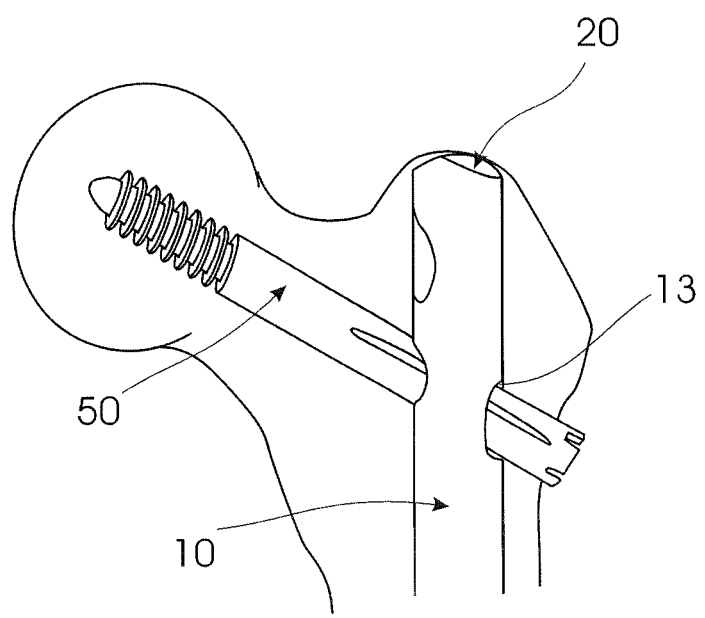
FIG. 5 is a side view of an intramedullary nail in a femur.

FIGS. 4 and 5 illustrate embodiments in which the implant is an intramedullary femur nail already implanted from the proximal end of the femur into the medullary channel of the femur, wherein a locking screw 50 is inserted through the transverse bore 13 of the nail and into the femur head.

The locking screw 50 comprises a threaded portion 51 adapted to be screwed into a bone and a trailing end 52 for an engagement with a driving tool. In these embodiments, the trailing end 52 has a crown-like shape with slots, wherein a corresponding driving tool may have a structure for engaging this crown to substantially rotate the screw while screwing in the screw into the bone. It will be understood that the trailing end of the locking screw may comprise a trailing end with a smooth end surface as described herein.

Further illustrated in FIGS. 4 and 5 is the aspect that the smooth end surface 20 at the trailing section 10 of the femur nail has a contour which substantially corresponds to the contour of the bone at the point of introduction of the nail, i.e. at the greater trochanter of the femur.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements, and the indefinite article "a" or "an" does not exclude a plurality.

The mere fact that the certain measures are recited in mutually different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A bone nail comprising:
a shaft extending along a longitudinal axis with a leading section adapted to be introduced first into a body during an implantation of the bone nail, and a trailing section adapted to be introduced last into the body during an implantation of the bone nail, the trailing end section terminating in an outwardly facing end face defined by a circumferential surface extending transverse to the longitudinal axis;
wherein the trailing section circumferential surface is continuously curved in a direction parallel to the longitudinal axis, the surfaces transverse to the longitudinal axis describe a sinusoidal-like waveform along the circumferential surface, having a depressed portion and an elevated portion in the direction parallel to the longitudinal axis, wherein a transition between the depressed portion and the elevated portion is a smooth transition.

2. The bone nail of claim 1, wherein the end surface is capable of transmitting rotational forces and translational forces from a medical device to the shaft when the medical device is coupled at the end face to the trailing section of the shaft.

3. The bone nail of claim 1, wherein the end face includes, with respect to the longitudinal axis, two or more depressed portions with elevated portions between the two or more depressed portions, respectively.

4. The bone nail of claim 3, wherein the bone nail is an intramedullary nail comprising a through bore for receiving a locking screw, the through bore extending through the shaft in a direction transverse to the longitudinal axis direction of the shaft.

5. The bone nail of claim 4, wherein a deepest point of each depressed portion extends along a transverse axis parallel with the axis of the through bore.

6. The bone nail of claim 3, further comprising a bone screw for locking the bone nail when implanted.

7. The bone nail of claim 1, wherein the end face corresponds to a shape of an outer bone surface at an intended implantation site so that the end face of the bone nail is flush with the bone surface surrounding the end face when the bone nail is inserted into the bone.

8. The bone nail of claim 1, further comprising an axial bore in the trailing section, the bore extending in a longitudinal axis direction of the shaft and including an inner thread for releasably fixing a medical device.

9. The bone nail of claim 1, further comprising a medical device comprising an implant engagement portion with a contact surface which corresponds to the end surface at the trailing section of the bone nail.

10. The bone nail of claim 1 wherein the nail trailing section has three elevated portions and three depressed portions forming a wave with a peak to peak amplitude of between 2.5 and 3.8 mm.

11. A bone nail comprising:
a longitudinally extending shaft having a longitudinal axis with a leading section adapted to be introduced first into a body during an implantation of the bone nail, and a tubular trailing section adapted to be introduced last into the body during an implantation of the bone nail, the tubular trailing section having a hollow interior with an open end, the hollow interior surrounded by a cylindrical wall defining an end face surrounding the open end, the end face having outwardly facing surfaces extending transversely to the longitudinal axis; and
wherein the outwardly facing surfaces of the tubular trailing section end face has, in a direction parallel to the longitudinal axis, at least one depressed portion and at least one elevated portion, wherein a transition between the depressed portion and the elevated portion is a smooth transition defining a sinusoidal waveform along a circumference of the end face.

12. The bone nail of claim 11, wherein the end face is capable of transmitting rotational forces and translational forces from a medical device to the shaft when the medical device is coupled at the end face to the trailing section of the shaft.

13. The bone nail of claim 11, wherein the end face includes at least two depressed portions with elevated portions between the at least two depressed portions, the depressed portions and elevated portion connected by the sinusoidal waveform transition.

14. The bone nail of claim 11, wherein the bone nail is an intramedullary nail comprising a through bore for receiving a locking screw, the through bore extending through the shaft in a direction transverse to the longitudinal axis of the shaft.

15. The bone nail of claim 11, wherein the hollow interior is an axial bore in the trailing section, the bore extending along the longitudinal axis of the shaft and including an inner thread for releasably fixing a medical device.

16. The bone nail of claim 11 wherein the nail trailing section has three elevated portions and three depressed portions forming the sinusoidal waveform transition with a peak to peak amplitude of between 2.5 and 3.8 mm.

* * * * *